United States Patent [19]
Trout

[11] Patent Number: 6,087,352
[45] Date of Patent: Jul. 11, 2000

[54] USE OF ZERANOL TO MODULATE REPRODUCTIVE CYCLES

[76] Inventor: William E. Trout, 1102 S. Jacobi Rd., Greenfield, Ind. 46140

[21] Appl. No.: 09/374,776

[22] Filed: Aug. 16, 1999

Related U.S. Application Data
[60] Provisional application No. 60/096,731, Aug. 17, 1998.

[51] Int. Cl.$^7$ .................................................. A61K 31/56
[52] U.S. Cl. ............................................................ 514/178
[58] Field of Search ............................................ 514/178

[56] References Cited

U.S. PATENT DOCUMENTS

| | | | |
|---|---|---|---|
| 3,989,828 | 11/1976 | Aries | 424/240 |
| 4,192,870 | 3/1980 | Grandadam et al. | 424/240 |
| 4,239,772 | 12/1980 | Shipchandler . | |
| 4,443,470 | 4/1984 | Hodge et al. . | |
| 4,886,899 | 12/1989 | Jacobs . | |
| 5,210,225 | 5/1993 | Moimas et al. | 539/270 |
| 5,314,882 | 5/1994 | Pantic et al. . | |
| 5,593,978 | 1/1997 | Jacobs et al. . | |
| 5,674,892 | 10/1997 | Giese et al. . | |
| 5,728,726 | 3/1998 | Giese et al. . | |

OTHER PUBLICATIONS

Deutscher, G.H., et al., "Time of Zeranol Implantation on Growth, Reproduction and Calving of Beef Heifers", J. Anim. Sci. 62:875–886, 1986.

Staigmiller, R.B., et al., "Growth and Reproductive Traits in Beef Heifers Implanted with Zeranol", J. Anim. Sci., 57:527–534, 1983.

Frank, M., et al., "A Study of Prostaglandin $F_{2\alpha}$ as the Luteolysin in swine: III Effects of Estradiol Valerate on Prostaglandin F, Progestins, Estrone and Estradiol Concentrations in the Utero–Ovarian Vein of Nonpregnant Gilts", Prostaglandins 14:1183–1196, 1977.

Kraeling, R., et al. "Prostaglandins–Induced Regression of Porcine Corpora Lutea Maintained by Estrogen", Prostaglandins 9:459–462, 1975.

Mirocha, C., et al., Zearalenone. In: J.V. Rodricks, C.W. Hessltine and M.A. Mehlam (eds.) Micotoxins in Human and Animal Health. Pathotox Publications Inc., Forest Park South, Il. 345–364, 1977.

Love, R.J., et al. "Seasonal effects on fertility in gilts and sows", J. Reprod. Fertil. (Suppl. 48):191–206, 1993.

Geisert, R.D., et al. "Length of pseudopregnancy and pattern of uterine protein release as influenced bt time and duration of oestrogen administration in the pig", J. Reprod. Fertil. 79:163–172, 1987.

Zavy, M.T., et al., "Estrogen–Induced Pseudopregnancy in Gilts: Its Use in Estrus Synchronization and Subsequent Influence on Litter Response", Theriogenol. 30:721–732, 1988.

Guthrie, H.D., "Estrous Synchronization and Fertility in Gilts Treated with Estradiol–Benzoate and Prostaglandin $F_{2\alpha}$", Theriogenol. 4:69–75, 1975.

Pusateri, A.E., et al. "Maternal Recognition of Pregnancy in Swine. 1. Minimal Requirement for Exogenous Estradiol–17βto Induce Either Short or Long Pseudopregnancy in Cycling Gilts", Biol. Reprod. 55:582–589, 1996.

Stob, M. et al., "Isolation of an Anabolic, Uterotrophic Compound from Corn infected with *Gibberella zeae* "Nature 196:1318, 1962.

Lindsay, D.G., "Zeranol–A 'Nature–Identical' Oestrogen?", Fd. Chem. Toxic. 23:767–774, 1985.

Etienne, M. and Jemmali, M., "Effects of Zearalenone (F2) on Estrous Activity and Reproduction in Gilts", J. Anim. Sci. 55:1–10, 1982.

Young, L.G. and King, G.J., "Low Concentrations of Zearalenone in Diets of Mature Gilts", J. Anim. Sci. 63:1191–1196, 1986.

Flowers, B. et al., "A Comparison of Effects of Zearalenone and Estradiol Benzoate on Reproductive Function During the Estrous Cycle in Gilts", J. Anim. Sci. 65:1576–1584, 1987.

Katzenellenbogen, B., et al., "Zearaenones: Characterization of the Estrogenic Potencies and Receptor Interactions of a Series of Fungal β–Resorcylic Acid Lactones", Endocrinol. 105:33–40, 1979.

Denzer, et al., "Evalution of Growth, Carcass Traits and Reproduction Organs of young Boars in Response to Zeranol Implantation", J. Anim. Sci. 62:1164–1171, 1986.

Brown, R.G., Ralgro Manual: Toxicology and Tissue residues of Zeranol. International Mineral and Chemical Corp. (Pub. Date Unknown).

Weekley, K.A.,"Nutritional management, breed of sire and zeranol effects on growth and reproductive traits in Bos taurus x Bos indicus beef heifers", M.S. Thesis, University of Florida 1991 (Title only, no abstract).

Khodabandeholu, H., et al. "Investigations on the occurence and content of oestrogenic activity in cattle feed in the state of Central Hessia, Germany", Deutsche Tieraerztliche Wochenschrift, 104:291–294, 1997 (Abstract).

Vanyi, A., et al., "Reproductive disorders due to F–2 and T–2 toxins in large scale pig farms", Magyar Allatorvosok Lapja, 50:424–430, 1995 (Abstract), Biological Abstract 100:8(127650).

Robert G., et al. "More important mycotoxicoses in pigs. Comprehensive clinico–pathological communication", Magyar Allatorvosok Lapja, 50:407–420, 1995 (Abstract), Biological Abstract 100:8(127649).

Etienne, M., et al. "Effects of zearalenone or glucosinolates in the diet on reproduction in sows: A review", Livestock Production Science, 40:99–113, 1994 (Abstract).

(List continued on next page.)

*Primary Examiner*—Raymond Henley, III
*Attorney, Agent, or Firm*—Jones & Askew, LLP

[57] ABSTRACT

This invention relates to a method for modulating the function of the reproductive system in female animals, especially farm animals, and specifically in horses and pigs, by administering an effective amount of zeranol. Specifically, this invention provides a method for maintaining corpus luteum function, especially in pigs and horses, by administering an effective amount of zeranol.

12 Claims, 4 Drawing Sheets

OTHER PUBLICATIONS

Marshall, T.T., et al. "Effects of zeranol on postweaning development and reproduction of beef heifers", J Dairy Sci, 72:464–465, 1989 (Title only, no abstract).

Khodabandehlou, H., et al., "Investigation of oestrogenic activity in cattle feeds in Central Hessia, Germany", Deutsche Tierarztliche Wochenschrift, 104:291–294, 1997 (Abstract).

Kramer, R., et al., "Free and conjugated levels of zearalenone in ewes mated on grass–dominant pasture or chicory", Proceesings of the New Zealand Society of Animal Production, 57:190, 1997 (Abstract).

Lusky, K., et al., "Simultaneous administration of the mycotoxins ochratoxin A and zearalenone to pigs in the feed. Effect on health, and tissue residues", Tierarztliche Umschau, 52:212–216, 221, 1997 (Abstract).

Renaville, R., et al., "Aspects on the use of anabolic steroids in animal production", Scientific conference on growth promotion in meat production. Proceedings, Brussels, Belgium, Nov. 29 to Dec. 1, 1995, 63–86, 1996 (Abstract).

Hargrove, D.D., "Use of growth promotions in replacements heifers", In Factors affecting calf crop., Editor, Fields, M.J., et al. pp. 91–104, 1994, Boca Raton, Florida (Abstract).

Williams, K.C., et al., "Effect of the mycotoxins, nivalenol and zearalenone, in maize naturally infected with Fusarium graminearum on the performance of growing and pregnant pigs", Australian Journal of Agricultural Research, 45:1265–1279, 1994 (Abstract).

Wolf, H., et al., "Observation on the effect of Fusarium toxins on fertility and litter size in sows.", Monatshefte fur Veterinarmedizin, 49:207–211, 1994 (Abstract).

Towers, N.R., "Zearalenone induced infertility in sheep", Publication–Veterinary Continuing Education, Massey, Proc. 22seminar, Sheep & Beef Cattle Soc., 145:159–178, 1992 (Abstract).

Kirkwood, R.N., et al., "The influence of zeranol implantation on growth and reproduction in heifers", Canadian Journal of Animal Science, 71:1253–1256, 1991 (Abstract).

Makarechian, M., et al., "Effect of postweaning implantation of zeranol and dietary energy level on growth and reproductive performance of replacement beef heifers", Canadian Journal of Animal Science, 71:265–270, 1996 (Abstract).

Libal, G.W., "Feeding sows to maximize reproductive and lactation capabilities", Swines nutrition (edited by Miller, E., et al.), Nutrition Abstract & Reviews: Series B Livestock Feds & Feeding, 62:527–555, 1991 (Abstract).

Moran, C., et al., "The effect of chronic exposure to androgens and oestrogens on development of mammary glands and reproduction tracts in heifers", 11th International Congress on Animal Reproduction and Artifical Insemination, University College Dublin, Ireland, Jun. 26–30, 4:3, 1988 (Abstract).

Kordic, B., et al., "Effect of low doses of the mycotoxin zearalenone on the reproductive characteristics of pigs", Veterinarski Glasnik, 44:151–155, 1990 (Abstracts).

Cohen, R.D.H., et al., "Effect of repeated implantation with zeranol from birth or weaning on growth and reproduction in beef heifers", Canadian Journal of Animal Science, 67(1) 37–42, 1987 (Abstract).

Yang, H.H., et al., "Effects of zearalenone and/or tamoxifen on swine and mink reproduction", J. Appl Toxicol, 15:223–32, 1995 (Abstract).

Ito, Y., et al., "Effects of neonatal administration of zearalenone on the reproductive physiology of female mice", J Vet Med Sci, 56:115–9, 1994 (Abstract).

Kordic, B., et al., "Experimental study of the effects of known quantities of zearalenone on swine reproduction", J. Environ Pathol Toxicol Oncol, 11:53–5, 1992(Abstract).

Rainey, M.R., et al., "Prepubertal exposure to dietary zearalenone alters hypothalamo–hypothalamo function but does not impair postpubertal reproductive function of gilts", J Anim Sci, 68:2015–22, 1990 (Abstract).

Smith, J.F., et al., "Reproductive performance of Coopworth ewes following oral doses of zeaealenone before and after mating", J Reprod fertil, 89:99–106, 1990(Abstract).

Green, M.L., et al., "Effect of prepubertal consumption of zearalenone on puberty and subsequent reproduction of gilts", J Anim Sci, 68:171–8, 1990 (Abstract).

Moran, C., et al., "Effects of oestradiol, zeranol or trenbolone acetate implants on puberty, reproduction and fetility in heifers", J Reprod fertil, 89:527–36, 1990 (Abstrcat).

Kuiper–Goodman, T., et al., "Risk assessment of the mycotoxin zearalenone", Regul Toxicol Pharmacol, 7:253–306, 1987 (Abstract).

Deschamps, J.C., et al., "Effects of zerznol on reproduction in beef bulls: luteinzing hormone, follicle stimulating hormone, and testosterone secretion in response to gonadotropin–releasing hormone and human chorionic gonadotropin", AM J Vet Res, 48:31–6, 1987 (Abstract).

Deutscher, G.H., et al., "Time of zeranol implantation growth, reproduction and calving of beef heifers", J Anim Sci. 62:875–86, 1986 (Abstract).

Becci, P.J., et al. "Combined two–generation reproduction–teratogenesis study of zearalenone in the rat", J Appl Toxicol, 2:201–6, 1982 (Abstract).

Staigmiller, R.B., et al., "Growth and reproductive traits in beef heifers implaned with zeranol"J Anim Sci, 57:527–34, 1983 (Abstract).

van Logten, M.J., et al., "Toxicological aspects of the use of hormones as anabolic agents (author's transl)", Tijdschr Diergeneeskd, 106:353–66, 1981 (Abstract).

Etienne, M., et al., "Effects of feeding corn infested by Fusarium to sows", CR Seances Acad Sci D, 288:779–82, 1979 (Abstract).

Chang, K., et al., "Effects of the mycotoxin zearalenone on swine reproduction", AM J Vet Res, 40:1260–7, 1979 (Abstract).

Prichard, D.L., et al., "Effects of creep feeding, zeranol implants and breed type on beef production: I. Calf and cow performance", J Anim Sci, 67(3):609–16, 1989 (Abstract).

Young, L.G., et al., "Effects of feeding zearalenone to sows on rebreeding and pregnancy", J Anim Sci, 68(1):15–20, 1990 (Abstract).

USE OF ZERANOL TO MODULATE REPRODUCTIVE CYCLES

PRIOR RELATED APPLICATION

This application claims priority to U.S. Provisional Patent Application Ser. No. 60/096,731 filed Aug. 17, 1998.

TECHNICAL FIELD

This invention relates to a method for modulating the function of the female reproductive system in animals, especially farm animals, and specifically in pigs and horses, by administering an effective amount of zeranol. Specifically, this invention provides a method for inducing pseudopregnancy, maintaining pregnancy, and maintaining progesterone synthesis and/or secretion from the corpus luteum, especially in pigs and horses, by administering an effective amount of zeranol.

BACKGROUND OF THE INVENTION

The control of estrus cycle synchronization in animals is desirable for many reasons. The timing of fertility and mating in animals is influenced by many factors, such as puberty onset, seasonal conditions, diet, photoperiod, heat, stress, crowding, transportation, lactation, recovery from previous pregnancy, recovery from lactation, and a variety of hormonal, neuroendocrine and immunological factors. In farm animals, the ability to control the estrus cycle directly affects the efficiency of animal husbandry and the cost of animal products. Some domesticated animals, such as horses, are raised for racing and other competitive events. Race horses enter the racing season based on age. Animals born early in a year will be stronger and larger than horses born later in the season. What is needed is a method to control the estrous cycle in horses so that the timing of fertility may be selected.

At present, no approved product or procedure exists for efficient and precise estrus synchronization in swine within the United States. In Europe, feeding of an oral progestin sold under the trademark REGU-MATE (Roussell UCLAF, France), is approved for estrus synchronization in mature cycling pigs. The oral progestin simulates the presence of functional corpora lutea (CL) as if the pig were pregnant. REGU-MATE must be supplied daily in the feed for about two weeks to achieve estrus synchronization. REGU-MATE is also quite expensive at a cost of about $2 per day per animal. Removal of REGU-MATE following 11 to 14 days of feeding results in the resumption of synchronous estrus cycles. REGU-MATE is not currently approved for use in the United States.

In mature cycling gilts and sows, estrus may be synchronized by breeding followed later by termination of the pregnancy with exogenous prostaglandin (PG), such as $PGF_2\alpha$. This is the so-called "breed to abort" strategy. Most commonly, this method is used to ensure full use of farrowing facilities. Producers usually breed more gilts and sows than will be required to fill the farrowing facilities for a particular farrowing group. Once enough females have remained pregnant through days 25 to 30 of gestation, the producer terminates the excess gilt pregnancies with PG to regress the CL, the progesterone secreting structure of the ovary. These females then return to estrus and are bred to fit into a subsequent farrowing group.

When producers select their own market weight gilts as replacement breeding stock, a degree of estrous synchronization can be obtained by keeping the selected gilts isolated from mature boars until they are to be introduced into the breeding herd. Gilts are then relocated to the breeding facilities and allowed contact with mature boars. Within two weeks of the initiation of relocation and boar exposure, 40 to 70% of gilts will experience their pubertal estrus. However, if gilts have already experienced puberty, they will not display estrus in a synchronous manner. The older and more reproductively competent gilts become, the more likely they are to respond to relocation and boar exposure. However, older gilts are also more likely to have experienced spontaneous puberty and thus, not be synchronized by movement and boar exposure. Therefore, a long felt and unfulfilled need of producers is to begin relocation and boar exposure to induce estrus when gilts are still prepubertal, but old enough to be near the time of puberty, i.e. peripubertal.

Producers can combine the movement and boar exposure strategy described above with the administration of a combination of pregnant mare serum gonadotropin (PMSG) and human chorionic gonadotropin (hCG), sold under the name PG600 (Intervet, Inc., Millsboro, Del.), which is approved for use in swine. A high percentage of prepubertal gilts display estrus and ovulate following PG600 administration and boar exposure. Using PG600, producers can work with younger gilts, which are not as likely to have already experienced puberty. However, most producers prefer not to breed at the PG600-induced estrus due to a reduction in litter size in these gilts. Instead, producers wait and breed PG600-treated gilts at their second estrus. Unfortunately, many prepubertal gilts which are induced to display estrus and ovulate with PG600 fail to display subsequent estrus in a predictable manner. This variability increases production costs of raising pigs (feed costs, housing costs, breeding, etc.), thereby raising the price of meat and other products derived from swine. At present, swine producers have no good methods for synchronizing estrus and breeding in replacement females (gilts). What is needed is a tool that allows producers to group gilts to be bred and to reliably synchronize the occurrence of a highly fertile estrus. Such a method would decrease production costs, thereby decreasing the costs of meat and other products derived from pigs.

An additional problem for swine producers is that they often receive shipments of a number of replacement gilts sufficient to meet the breeding requirements of the next several weeks. These replacement gilts may come from the producer's own gilt multiplier herd or from a breeding stock company. If the gilts are near pubertal age at the time of receipt, the stress associated with shipping and mixing of these gilts often triggers pubertal estrus. The frequent result is that too many gilts are available for breeding during the first one to two weeks after receipt, while too few gilts are available three to four weeks after receipt. Variation in the age of the replacement gilts when they are received at the breeding facility adds to the difficulty. Between and within shipments, gilts may vary in age by two to three weeks. This variation in age produces a variable response of the gilts to boar exposure thereby increasing variation in the number of gilts available for breeding. At present, producers maintain a large pool of replacement gilts to ensure that a sufficient number of gilts will be available to meet their breeding targets. What is needed is a means to control estrus in a group of replacement gilts as they are received at the breeding facility. A method which would allow producers to reliably control the occurrence of a highly fertile estrus in gilts could potentially reduce the size of the gilt pool by 50%, resulting in savings in feed, facilities and labor.

A method of estrous synchronization would also be useful in sows. Following lactation, sows exhibit a degree of estrus synchronization, assuming that they are weaned after about day 17 of lactation and are in good body condition. Weaning removes the suckling-induced inhibition of pituitary gonadotropin secretion. The majority of sows display estrus within a week of the removal of the litter. However, many producers now employ early weaning strategies that wean the piglet from the dam as early as day 10 of age. While early weaning is good for the health of the piglets, this strategy increases stress on the sow, who has yet to recover from pregnancy and lactation, thereby causing variable return to estrus in sows following weaning from the litter. Accordingly, what is needed is a procedure which controls the return to estrus in sows following lactation. In early-weaned sows or in sows with poor body condition, it may be desirable to delay the return to estrus in order to allow the sow to recover from pregnancy and lactation.

Seasonal infertility in gilts and sows is another problem encountered by producers. Farrowing rates drop by 5 to 12% in females bred during the summer months (Love R. J., et al., 1993, J. Reprod. Fertil. (Suppl. 48):191–206). During this time, affected pigs fail to remain pregnant and they return to estrus within about 30 days of breeding. This is thought to be more an effect of long day lengths rather than of increased environmental temperatures, although both factors are involved. Data suggest that females bred during long days fail to recognize the pregnancy signals produced by the conceptuses on days 11 to 15 of pregnancy. Failure to recognize these signals results in loss of the pregnancy. What is needed is a way to mimic or augment the embryonic signals of pregnancy, thereby maintaining pregnancy in gilts and sows that are experiencing seasonal infertility.

In the pig, the CL must be maintained throughout the entire pregnancy or abortion results. PG can be administered at any time between days 14 and 90 of gestation with good return to estrus and good breeding success. However, many producers dislike using this methodology to synchronize estrus since an established pregnancy must be terminated. In order for the method to work, estrus must be detected, the female must be bred and she must become pregnant. What is needed is a method which is highly effective at producing synchronous estrous by inducing a pseudopregnancy, and does not involve breeding and abortion of an established pregnancy.

It has been known for many years that the life span of the pig CL can be extended by daily administration of high doses of estrogen (estradiol-17β, estradiol valerate or estradiol benzoate) on days 11 through 15 of the estrus cycle (Geisert R. D., et al., 1987, J. Reprod. Fertil. 79:163–172; Zavy, M. T., et al., 1988, Theriogenol. 30: 721–732; Guthrie, H. D. 1975, Theriogenol. 4:69–75; Pusateri, A. E. et al., 1996, Biol. Reprod. 55: 582–589). Days 11 through 15 of the estrous cycle are often referred to as the period of maternal recognition of pregnancy. On these days the pregnant pig receives embryonic hormonal signals, which maintain the CL and the pregnancy. If the dam does not receive these signals or if she does not recognize the pregnancy, her uterus secretes PG which destroys the CL, progesterone production ceases, and the pregnancy is lost. Very high doses of estrogen, injected intramuscularly on days 11 through 15 of the estrous cycle, are thought to mimic the embryonic signals produced during pregnancy and result in CL maintenance, i.e. pseudopregnancy. As a result of CL maintenance, serum progesterone concentrations remain elevated during pseudopregnancy. The CL in estrogen-induced, pseudopregnant pigs commonly persist for more than 60 days. However, the CL of pseudopregnant pigs remain sensitive to destruction by PG. Following PG administration, the CL die or regress and the pigs return to estrus within 3 to 7 days.

Fertility in gilts bred following an estrogen-induced pseudopregnancy has been reported to be very good (Zavy M. T., et al., 1988, Theriogenol. 30: 721–732; Guthrie, H. D. 1975, Theriogenol. 4:69–75). In fact, birth weights and postnatal survival were reportedly enhanced (Zavy M. T., et al., 1988, Theriogenol. 30: 721–732). Unfortunately, repeated administration of high dosages of estrogen poses additional health risks, such as cancer, to animals that receive estrogen and to the workers who administer estrogen. In addition, it is impractical and costly for swine producers to administer multiple injections of estrogen over a very narrow and specific number of days of the estrous cycle in order to induce pseudopregnancy. These methods, involving daily or repeated administration of estradiol, are impractical, labor intensive, and expensive to practice in large numbers of animals such as farm animals. In addition, such repeated administration of estradiol can be stressful to animals, thereby affecting reproduction and immunity. Producers of animals need more convenient and affordable methods to synchronize estrus cycles. What is needed is a simple and economical method for inducing pseudopregnancy in animals such as pigs, so that the CL of these pseudopregnant animals could be destroyed with PG, resulting in a predictable return to a highly fertile estrus.

In addition to estradiol, the compound zearalenone has been shown to extend the life span of the CL of the pig when fed. The fungus *Fusarium Rosium*, commonly found in moldy corn, produces zearalenone (Stob, M., et al., 1962, Nature 196:1318). Zearalenone has been demonstrated to have weak estrogenic properties (Lindsay, D. G. 1985, Fd. Chem. Toxic. 23: 767–774), possessing about 2% of the potency of estradiol-17β. However, when administered orally in the pig, the liver metabolizes zearalenone to α-zearalenol which possesses about 20% of the potency of estradiol-17β. Zeranol is a different compound from α-zearalenol. Zearalenone will extend the life span of the CL when fed to pigs at a dose of 7 to 20 mg/day during the time of maternal recognition of pregnancy, i.e., days 11 to 15 of the estrous cycle (Etienne, M. and Jemmali, M., 1982, J. Anim. Sci. 55: 1–10; Young, L. G. and King, G. J., 1986, J. Anim. Sci. 63: 1191–1196; Flowers, B., et al., 1987, J. Anim. Sci. 65: 1576–1584).

Accordingly, what is needed is a method to modulate and synchronize reproductive cycles in female animals, such as farm animals, and especially in pigs and horses. What is also needed is a method for inducing pseudopregnancy in animals, such as farm animals. Also needed is a method for maintaining the function of the CL and associated progesterone synthesis and/or secretion. This method should support uterine function thereby assisting in the maintenance of pregnancy. What is also needed is a method for controlling the timing of estrus and insemination in animals such as farm animals. Also needed is a method for facilitating controlled insertion of groups of prepubertal and peripubertal gilts into a breeding herd. A method for synchronization of estrus and breeding of sows following lactation is also needed. Also needed is a method for decreasing periods of infertility and returning animals to a fertile state. Such a method should decrease the costs of producing animals by decreasing the costs associated with prolonged housing, feeding, and unsuccessful attempts at reproduction, thereby reducing costs of products derived from animals.

SUMMARY OF THE INVENTION

The present invention solves these problems by providing a method which effectively modulates the reproductive cycles of female animals through administration of zeranol or derivatives of zeranol. While not wanting to be bound by the following statement, it is believed that zeranol treatment maintains the function of the CL and associated progesterone synthesis and/or secretion. The method of the present invention induces a state of pseudopregnancy and facilitates the maintenance of pseudopregnancy and pregnancy in animals. The method of the present invention also helps synchronize the timing of estrus and insemination in animals.

In one embodiment, the method of the present invention is used in horses. This method permits control of the timing of estrus cycles in horses, thereby facilitating timing of insemination. Practice of this method permits creation of a pseudopregnant condition in mares. Practice of this method also assists in maintenance of pregnancy in mares. These effects on the reproductive system of mares enable predictability of the timing of successful insemination and of the timing of birth of the offspring. An advantage of this method is that costs associated with breeding are reduced. Another advantage of this method is that horses bred for racing may be born early in the season, thereby maximizing their growth potential before onset of the racing season.

In another embodiment, the method of the present invention is used in pigs, specifically gilts and sows. This method allows for the controlled insertion of groups of prepubertal and peripubertal gilts into a breeding herd, thereby reducing the costs of labor and the costs associated with maintaining replacement females. In sows, the method of the present invention facilitates the synchronization of estrus and breeding following lactation. In this manner, estrus of the entire farrowing group is controlled such that sows can be easily maintained as a group within the management scheme. The method of the present invention provides producers with the option of delaying estrus in their sows in order to allow sows to recover from the rigors of lactation. Estrus of gilts can also be synchronized to that of the sows in a farrowing group to facilitate the replacement of culled sows. Finally, in both gilts and sows, the estrus synchronization scheme controls the time of ovulation. Therefore, insemination can be timed more precisely, reducing semen costs, lost breeding opportunities, and labor and feed costs associated with breeding.

The present invention stems from the discovery that zeranol, currently approved for use as a growth stimulant in cattle, maintains the function of the CL of the pig. Zeranol, implanted subcutaneously (sc) in the ear within 11 days following estrus, prevented return to estrus and also prolonged progesterone secretion by the CL. The CL of zeranol-implanted gilts regressed following the administration of $PGF_2$-$\alpha$ and gilts returned to estrus within 3 to 7 days. Thus, it appears that a sufficient dose of zeranol, if present during the period of maternal recognition of pregnancy in the pig, will render pigs pseudopregnant. This discovery facilitated development of the procedures of the present invention to synchronize reproductive cycles in animals, especially in pigs and horses.

Zeranol is manufactured from zearalenone and is the active component of a commercial product sold under the trademark RALGRO (Pitman-Moore, Inc., Northbrook, Ill.), used to enhance growth and feed efficiency in steers. Zeranol possesses weak estrogenic activity. Zeranol binds to the estrogen receptor with 14% of the affinity of estradiol-17$\beta$ (Katzenellenbogen, B., et al., 1979, Endocrinol. 105: 33–40). However, unlike zearalenone, zeranol is less potent when administered orally. When given orally, zeranol is metabolized by the liver to $\beta$-zearalanone which is only about 4% as potent as estradiol-17$\beta$ (Lindsay, D. G., 1985, Fd. Chem. Toxic. 23: 767–774). We are unaware of any reports concerning the effects of zeranol administered either orally, by injection, or by implantation, upon CL function in any species, including pigs and horses. Zeranol implants have been administered to male pigs (boars) with no obvious effects on their reproductive physiology (Denzer, et al., 1986. J. Anim. Sci. 62:1164–1171).

Zeranol may be administered orally, topically or parenterally. It is to be understood that various methods known to one of ordinary skill in the art may be used for administration through any route. It is to be understood that zeranol may be administered alone, or in combination with other substances. Some of these substances may affect the reproductive system and include but are not limited to the following: hCG; PG600; PMSG (e (equine) CG); PG, $PGF_2\alpha$; hypothalamic peptides, including but not limited to, gonadotropin releasing hormone (GnRH); neuropeptide Y, other hypophysiotropic substances and analogs thereof; gonadotropins including luteinizing hormone (LH) and follicle stimulating hormone (FSH); catecholamines; estrogen; progesterone; analogs thereof; and combinations thereof. Dosages of these substances which affect the reproductive system are known to one of ordinary skill in the art. Gonadotropins may be administered concurrently with or before zeranol administration, and may optionally be followed by PG administration after zeranol administration.

During our initial experiments, we found that implants containing from 6 to 72 mg of estradiol-17$\beta$ failed to maintain the CL of gilts. These implants were inserted subcutaneously under the skin of the ear prior to day 10 of the estrous cycle so that the estrogen would be present on days 11 to 15 of the cycle, the critical days when injections of estrogen will induce pseudopregnancy (Geisert R. D., et al., 1987, J. Reprod. Fertil. 79:163–172; Zavy M. T., et al., 1988, Theriogenol. 30: 721–732; Guthrie, H. D. 1975, Theriogenol. 4:69–75; Pusateri A. E. et al.,1996, Biol. Reprod. 55: 582–589). In contrast, treatment of gilts at this time with subcutaneous implants containing 12 mg of zeranol resulted in about 50% pseudopregnancy. In addition, treatment with implants containing 24 or 36 mg resulted in an incidence of pseudopregnancy between 85 and 100%. These unexpected results are even more surprising when one considers that zeranol has only about 14% of the potency of estradiol-17$\beta$, and that a 36 mg zeranol implant releases only about 600 ug of zeranol per day (Brown, R. G., Ralgro Manual: Toxicology and Tissue Residues of Zeranol. International Minerals and Chemical Corp.). Thus, a 36 mg zeranol implant would theoretically release the equivalent of about 84 ug of estradiol-17$\beta$ per day. Pusateri et al. reported that an average daily dose of 496 ug of estradiol-17$\beta$ (4 ug/kg body weight in gilts averaging 124 kg) was required to render 50% of gilts pseudopregnant (Pusateri, A. E., et al.,1996, Biol. Reprod. 55: 582–589). We found that a 12 mg implant of zeranol, releasing about 200 ug of zeranol per day, made 50% of gilts (weighing 109 kg) pseudopregnant. A dose of about 200 ug of zeranol has an estrogenic potency of about 28 ug of estradiol-17$\beta$. Thus, the dose of zeranol which we found to be effective at inducing 50% pseudopregnancy has about 1/18th of the estrogenic potency of the dose of estradiol-17$\beta$ which is required to induce 50% pseudopregnancy. In other words, zeranol appears to be about 18 times more potent at maintaining the function of the pig CL than it should be based upon its estrogenic potency.

Through practice of the present invention, replacement gilts, whether pre- or post-pubertal, are brought into the breeding herd in a synchronized manner without the need for daily exposure to a boar and observation for estrus as is required by current practice. During weeks 2 to 17 of zeranol-induced pseudopregnancy, the producer can induce estrus by intramuscular (im) administration of prostaglandin $F_2\alpha$ or analogs thereof. When administered as implants, zeranol is preferably administered once in a range of about 0.01 to 150 mg, with a preferred range of about 0.1 to 80 mg, and a more preferred range of about 1.0 to 40 mg. When zeranol is administered orally in swine, it is preferably administered daily in a dosage range from about 0.1 mg to 1000 mg, with a preferred range of about 0.5 mg to 300 mg, and a more preferred range of about 1.0 mg to 150 mg. Whether administered as an implant or orally, zeranol should be administered so that it will be present during the period of maternal recognition of pregnancy, days 11–15 of the estrous cycle, in order to induce pseudopregnancy. Prostaglandin $F_2\alpha$ (PG) is administered in a range of about 1 to 100 mg/injection, with a preferred range of approximately 5 to 20 mg/injection. Two injections of about 10 mg/injection at an interval of 4 to 6 hours have been found to be adequate, and may be repeated if necessary. Gilts are then monitored for estrus and bred following administration of PG.

Return to estrus following lactation is controlled in sows through the practice of the present invention. Sows are treated with hCG im (preferred range of between about 150 and 10,000 IU, with a more preferred range of between about 250 and 5000 IU, and a most preferred range of approximately 500 to 4000 IU) and treated with zeranol at farrowing. When implanted, zeranol is administered in a range of about 0.01 to 150 mg, with a preferred range of about 0.1 to 80 mg, and a more preferred range of about 1.0 to 40 mg. When zeranol is administered orally in swine, it is preferably administered daily in a dosage range from about 0.1 mg to 1000 mg, with a preferred range of about 0.5 mg to 300 mg, and a more preferred range of about 1.0 mg to 150 mg. Zeranol administration may be delayed for several days after hCG administration if desired. Again, zeranol should be administered so that it will be present during the period of maternal recognition of pregnancy, days 11–15 of the estrous cycle, in order to induce pseudopregnancy. Estrus can be induced in sows by PG administration at 2 to 17 weeks of pseudopregnancy. PG is administered in a range of about 1 to 100 mg/injection, with a preferred range of approximately 5 to 20 mg/injection. Two injections of about 10 mg/injection at an interval of 4 to 6 hours have been found to be adequate, and may be repeated if necessary.

Practice of the method of the present invention provides numerous benefits and advantages. Replacement gilts can be moved to the breeding facility and treated with the method of the present invention as a group on a single day. Gilts from this group can then be induced to estrus as required. Gilts need not be checked daily for estrus, nor their estrus cycles tracked prior to breeding. Older and larger gilts can be induced to estrus and bred before the smaller and less mature females in a group of replacement females. The number of gilts induced to estrus can be controlled to match the number of culled sows requiring replacement at any given time. Nutritional manipulations designed to increase ovulation rate and to improve embryonic survival can be applied to synchronized groups of gilts. Sows differing in their time of farrowing can be returned to estrus and be bred in a more synchronized manner. Early-weaned sows can be allowed to recover from the stress of lactation before being bred again. Sows in poor body condition can have estrus delayed to coincide with the next farrowing group to allow better recovery before being bred again.

Accordingly, an object of the present invention is to provide a method for modulating the function of the female reproductive system through administration of a composition comprising an effective amount of zeranol.

Accordingly, an object of the present invention is to provide a method for maintaining the corpus luteum in animals.

Another object of the present invention is to provide a method for maintaining progesterone synthesis and secretion from the corpus luteum in animals.

An object of the present invention is to provide a method for maintaining the corpus luteum in horses.

Another object of the present invention is to provide a method for maintaining the corpus luteum in pigs.

Yet another object of the present invention is to provide a method for maintaining induced corpora lutea in prepubertal pigs.

Another object of the present invention is to provide a method for maintaining progesterone synthesis and secretion from the corpus luteum in pigs.

Yet another object of the present invention is to provide a method for maintaining pregnancy in animals.

Still another object of the present invention is to provide a method for inducing pseudopregnancy in animals.

Another object of the present invention is to provide a method for synchronizing reproductive cycles in animals.

It is an object of the present invention to provide a method for inducing pseudopregnancy in farm animals.

Yet another object of the present invention is to provide a method for synchronizing reproductive cycles in farm animals.

Still another object of the present invention is to decrease seasonal infertility in animals, especially swine.

It is further a specific object of the present invention to provide a method for inducing pseudopregnancy in pigs.

It is an object of the present invention to provide a method for synchronizing reproductive cycles in pigs.

Another object of the present invention is to provide a method for controlling the timing of estrus and insemination in animals.

Another object of the present invention is to provide a method for controlling the timing of estrus and insemination in farm animals.

It is further a specific object of the present invention to provide a method for controlling the timing of estrus and insemination in both gilts and sows.

It is another object of the present invention to provide a method for controlled insertion of groups of prepubertal and peripubertal gilts into the breeding herd.

An advantage of the present invention is that it reduces costs associated with animal husbandry and with maintaining replacement female pigs.

Another object of the present invention is to provide a method for synchronization of estrus and breeding of sows following lactation.

An advantage of the present invention is that it permits producers to delay estrus in sows in order to allow the sows to recover from the rigors of lactation.

Another advantage of the present invention is that reduces production costs, thereby decreasing the costs of products derived from farm animals, especially swine.

These and other objects, features and advantages of the present invention will become apparent after a review of the following detailed description of the disclosed embodiments.

BRIEF DESCRIPTION OF THE FIGURES

FIG. 1 shows a synchronization protocol for prepubertal and peripubertal gilts. 500 IU of hCG can be administered as early as 4 months of age to induce ovulation. Alternatively, PG600 can be used to induce ovulation in older gilts (i.e., 5–8 months of age). Whether administered orally or as an implant, zeranol should be administered so that it will be present during the period of maternal recognition of pregnancy, days 11–15 of the induced estrous cycle, in order to induce pseudopregnancy. Zeranol-induced pseudopregnancy is later terminated with PG. About 85%–90% of gilts will display estrus within 3–7 days following treatment with PG.

FIG. 2 shows a synchronization protocol for cycling gilts and sows. Whether administered orally or as an implant, zeranol should be administered so that it will be present during the period of maternal recognition of pregnancy, days 11–15 of the estrous cycle, in order to induce pseudopregnancy. Zeranol-induced pseudopregnancy is later terminated with PG. Gilts and sows will display estrus within 3–7 days following treatment with PG.

FIG. 3 displays a synchronization protocol for lactating sows. hCG or a combination of PMSG/hCG is injected at farrowing to induce ovulation. Whether administered orally or as an implant, zeranol should be administered so that it will be present during the period of maternal recognition of pregnancy, days 11–15 of the estrous cycle, in order to induce pseudopregnancy. Zeranol-induced pseudopregnancy is later terminated with PG. Sows display estrus within 3–7 days after treatment with PG.

DETAILED DESCRIPTION OF THE INVENTION

The term "zeranol" is synonymous with zearanol, α-zearalanol, zearalanol, RALGRO, P-1496, 3,4,5,6,7,8,9, 10,11,12-Decahydro-7,14,16-trihydroxy-3-methyl-1H-2-benzoxacyclotetradecin-1-one; (3S,7R)-3,4,5,6,7,8,9,10,11, 12-decahydro-7,14,16-trihydroxy-3-methyl-1H-2-benzoxacyclotetradecin-1-one; 6-(6,10-dihydroxyundecyl)-beta-resorcylic acid, mu-lactone; frideron; MK-188; ralabol; ralone; [3S-(3R*,7S*)]-3,4,5,6,7,8,9,10,11,12-decahydro-7, 14,16-trihydroxy-3-methyl-1H-2-benzoxacyclotetradecin-1-one; (3S,7R)-(+)-3,4,5,6,7,8,9,10,11,12-decahydro-7,14, 16-trihydroxy-3-methyl-1H-2-benzoxacyclotetradecin-1-one; including derivatives and analogs thereof.

The term "zearalenone" is synonymous with benzoxacyclotetradecin-1,7(8H)-dione; compound F-2; FES; (−)-zearalenone; trans-zearalenone; 6-(10-hydroxy-6-oxo-trans-1-undecenyl)-beta-resorcylic acid lactone; fermentation estrogenic substance; f-2 toxin, fusarium toxin; mycotoxin f2; ntoxin f2; (S)-Zearalenone; (10S)-zearalenone.

The term "pseudopregnancy" means a state of false pregnancy in which the function of the uterine endometrium resembles that of the pregnant uterus. In pseudopregnancy, the progesterone secretory function of the corpora lutea is maintained, thereby holding in abeyance the onset of the next estrus.

The term "gonadotropin" means any substance that supports gonadal function, such substances including but not limited to the following: chorionic gonadotropin; pituitary gonadotropin; luteinizing hormone; and follicle stimulating hormone.

The term "farrow" means to give birth to a litter of pigs.

The terms "farrowed, farrowing, and farrows" mean to give birth, for example, to a litter of pigs.

The term "gilt" means a young sow that has not farrowed.

The term "sow" means an adult female pig and adult females of several other types of animals.

Zeranol may be administered to a variety of animals, including but not limited to farm animals. Animals which may be treated with the method of the present invention to influence CL function include but are not limited to the following: pigs, feral pigs, and peccaries; other farm animals such as sheep, horses, race horses, and cattle; bears, hippopotami and other zoo animals such as lions, tigers, elephants, and rhinos; and laboratory animals, including rats, mice, hamsters, guinea pigs, and cats. The present method may be particularly useful for maximizing breeding potential of stud animals, exotic species and species that are difficult to reproduce in captivity.

Zeranol, together with acceptable carriers, can be administered as a composition through different routes. The composition may be given through standard routes of administration, including but not limited to oral, parenteral and topical. In general, the composition may be administered by topical, oral, rectal, vaginal, nasal or parenteral (for example, intravenous, subcutaneous, or intramuscular) routes. The composition may be in the form of a solid, liquid, cream, gel or aerosol. Examples of solid compositions include pills, creams, pellets, rods, and implantable dosage units. Pills may be administered orally. Other forms suitable for oral administration include wafers, seed, feed, meal, cereal, pellets and other suitable forms known to one of ordinary skill in the art. Preferred methods of administration are oral, topical and subcutaneous implants.

Zeranol may also be incorporated into sustained release matrices such as biodegradable polymers, the polymers being implanted in the vicinity where delivery is desired. A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The method of the present invention includes administration of a single dose, administration of repeated doses at predetermined time intervals, and sustained administration for a predetermined period of time. Zeranol may be administered in the form of implants which may be placed subcutaneously or intradermally, through injection, including but not limited to intradermal, intramuscular, subcutaneous, intraperitoneal, and intravascular injection, and also through transdermal, oral, nasal, and vaginal administration. Implants may be in the form of particles including microparticles and nanoparticles, pellets, SILASTIC (Dow Coming Corp., Midland, Mich.) tubes, rods, osmotic capsules, osmotic mini-pumps or other forms which may suggest themselves to one of ordinary skill in the art. Zeranol may be administered orally and also placed in the feed or water of animals. Zeranol administration may occur through various forms including but not limited to pellets, wafers, pills, emulsions including water-in-oil emulsions, water-in-oil-in-water emulsions and oil-in-water emulsions, suspensions, mixtures, solution, and in drinking water. It is to be understood that zeranol may be administered with any carrier acceptable in the veterinary industry and known to one of ordinary skill in the art.

When zeranol is administered as implants in swine, it is preferably administered once in a dosage range from about 0.01 mg to 150 mg, with a preferred range of about 0.1 mg to 80 mg, and a more preferred range of about 1.0 mg to 40 mg. When zeranol is administered to horses as an implant, it is preferably administered once in a range of about 0.01 to 800 mg, with a preferred range of about 1 to 500 mg, and a more preferred range of about 10 to 100 mg. It is to be understood that the present invention includes optional administration of more than one implant. When zeranol is administered orally in swine, it is preferably administered daily in a dosage range from about 0.1 mg to 1000 mg, with a preferred range of about 0.5 mg to 300 mg, and a more preferred range of about 1.0 mg to 150 mg. When zeranol is administered orally to a horse, it is preferably administered daily in a dosage range from about 1 mg to 5000 mg, with a preferred range of about 5 mg to 2500 mg, and a more preferred range of about 10 mg to 1000 mg. It is to be understood that the present invention includes optional oral administration of zeranol at other than daily schedules. When zeranol is administered through other routes, such as transdermally, it is administered in an amount effective to modulate the function of the female reproductive system. It is to be understood that various methods known to one of ordinary skill in the art may be used for administration through any route. For example, zeranol may be administered transdermally using methods taught in U.S. Pat. No. 5,925,373, the entirety of which is incorporated herein by reference.

The dosage of the composition comprising zeranol and an acceptable carrier will depend on the particular composition used, and other factors such as the reproductive status, age and weight of the animal, and the route of administration. It is to be understood that zeranol may be administered as a composition in combination with other substances, as desired, to modulate reproductive cycles, including but not limited to the following: hCG; PG600; PMSG (e (equine) CG); prostaglandin F2α (PG, $PGF_2\alpha$); hypothalamic peptides, including but not limited to, gonadotropin releasing hormone (GnRH), neuropeptide Y, other hypophysiotropic substances and analogs thereof; gonadotropins including luteinizing hormone (LH) and follicle stimulating hormone (FSH); catecholamines; estrogen; progesterone; analogs thereof; and combinations thereof.

It is to be understood that administration of zeranol may be preceded by administration of other substances. Zeranol administration may also be followed by administration of other substances. For example, in one embodiment of the present invention, gonadotropins may be administered concurrently with, or prior to, administration of zeranol. Animals receiving this treatment may subsequently be administered another substance, such as prostaglandin F2α. Gonadotropin administration induces ovulation. Zeranol administration maintains the pseudopregnant condition and supports the corpus luteum (or corpora lutea) produced after ovulation. PG administration may subsequently terminate the state of pseudopregnancy through deleterious effects on the corpus luteum. In another embodiment of the present invention, zeranol is administered to a pregnant animal to support pregnancy. In yet another embodiment of the present invention, zeranol is administered at selected days of the estrus cycle to induce a state of pseudopregnancy.

When gonadotropins are administered concurrently with or prior to the administration of zeranol, gonadotropins are administered in a dosage range of between about 150 and 10,000 IU, with a preferred range of between about 250 and 5,000 IU, and a more preferred range of 500 to 1,500 IU. Preferred gonadotropins are human chorionic gonadotropin (hCG), PMSG, a combination of PMSG and hCG, a combination of PMSG and human(h) CG (hCG) approved for use in swine and known as PG600 (Intervet, Inc., Millsboro, Del.). Gonadotropins may also be administered in a sequential manner before zeranol administration. For example, PMSG may be administered, followed by hCG hours or days later. For example, the administration of PMSG (800–1500 IU) followed 3 to 4 days later by hCG (500–1000 IU) will reliably induce ovulation and subsequent formation of CL in swine. A combined administration of PMSG (400–1200 IU) and hCG (200–600 IU) may also be used.

When prostaglandin-F2α (PG) or its analogues is administered after zeranol treatment, it is administered in any dose effective for termination of the function of the corpora lutea. PG may be administered at a dose of 1 to 100 mg/injection, with a preferred range of approximately 5 to 20 mg/injection. One effective administration in swine is two (2) 10 mg injections. The two injections may be spaced by a period of from about 3 to 8 hours, preferably 4 to 6 hours. Injections of PG may be repeated if necessary. The preferred method of administration is intramuscular injection. $PGF_2\alpha$ or its analogues are the preferred prostaglandins.

Subcutaneous administration of zeranol implants (0.01 to 150 mg, preferably 0.1 to 80 mg, more preferably 1 to 40 mg, sc in the ear, i.e., under the skin of the ear) renders female pigs pseudopregnant when implanted before day 11 of the estrous cycle, whether ovulation was induced or occurred naturally. The CL are maintained beyond their normal life span. Other methods of administration of zeranol cause pseudopregnancy at different times, depending on the age of the pig, its reproductive and lactational status, and the dosage and route of zeranol administration. In pigs with zeranol-maintained CL, estrus is induced by administering PG to cause regression of the CL. The pigs display estrus within 3 to 7 days following PG administration.

Combined hCG and Zeranol Treatment in Pre- and Peripubertal Gilts

Figure 1:
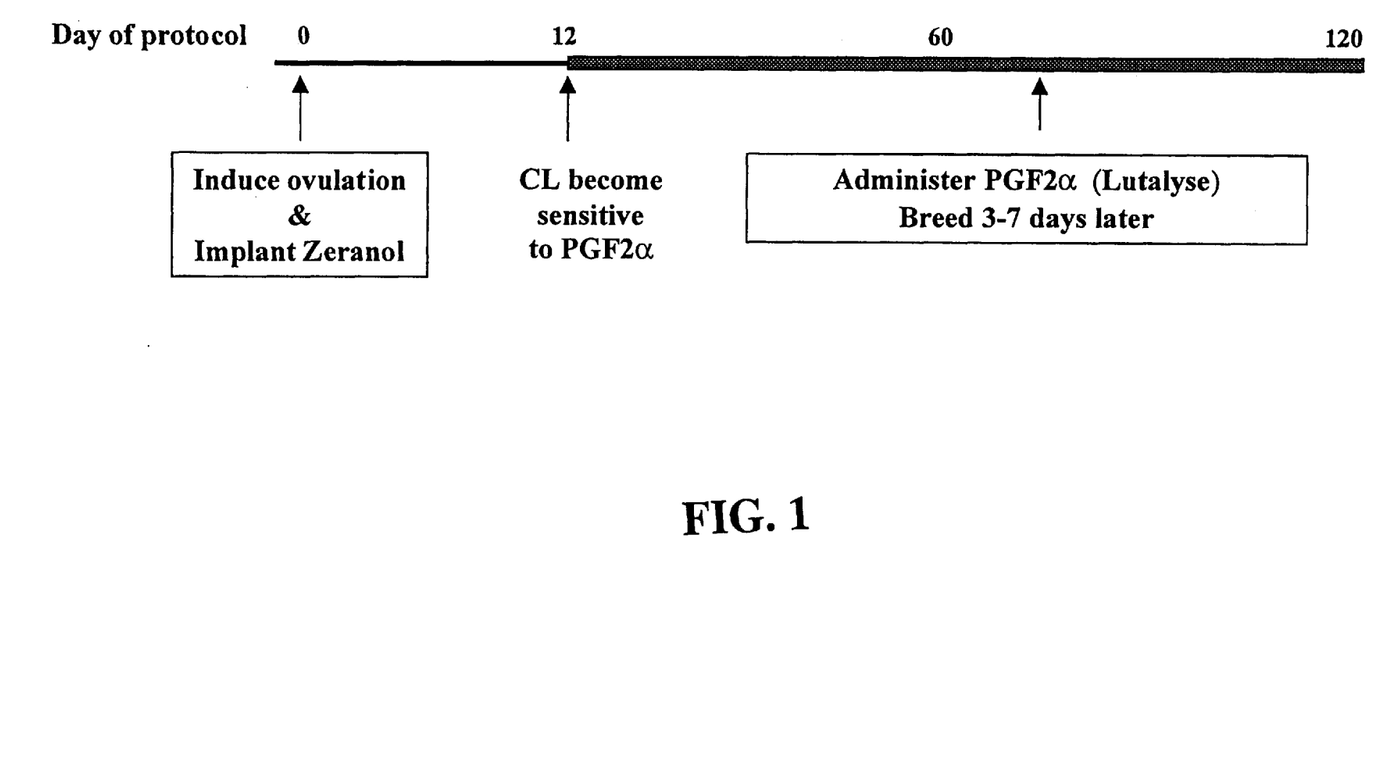

The present invention includes a novel combined regimen comprising treatment of pigs with hCG and zeranol (FIG. 1). The hormone hCG causes ovulation and zeranol maintains the newly formed CL. Treatment of prepubertal replacement gilts with this regimen facilitates ovulation and maintenance of the newly formed CL with concomitant progesterone secretion. Zeranol treatment also helps to ensure long pseudopregnancy (i.e. greater than 60 days). Prepubertal or peripubertal gilts are treated with hCG (preferred range of between about 150 and 10,000 IU, with a more preferred range of between about 250 and 5,000 IU, and a most preferred range of 500 to 1,000 IU). When zeranol is administered as an implant, it is preferably administered once in a range of about 0.01 to 150 mg, with a preferred range of about 0.1 to 80 mg, and a more preferred range of about 1 to 40 mg. When zeranol is administered orally, it is preferably administered daily in a dosage range from about 0.1 mg to 1000 mg, with a preferred range of about 0.5 mg to 300 mg, and a more preferred range of about 1.0 mg to 150 mg. Zeranol should be administered so as to be present during the period of maternal recognition of pregnancy (days 11–15 of the induced estrous cycle). The producer can administer PG, as two separate 5–10 mg injections spaced 4 to 6 h apart, at any time from 2 to 17 weeks following hCG induced ovulation to cause regression of the CL and return to estrus (FIG. 1). The females will experience estrus 3 to 7 days after PG and may then be bred.

One novel aspect of the method of the present invention is induction of ovulation and the formation of CL in prepubertal gilts and then maintenance of these induced CL with zeranol administration. It is to be understood that within the practice of the present invention, ovulation may be induced in prepubertal gilts by a variety of means. Currently, one of the cheapest methods is to administer gonadotropin, such as hCG, by injection. It may also be possible to utilize an effective hCG implant. It is believed that other compounds may induce ovulation in swine. These compounds include, but are not limited to the following: natural or recombinant luteinizing hormone (LH); GnRH, GnRH analogues or estrogens could be used to stimulate a surge of LH release by the gilt's own anterior pituitary gland; PMSG, alone or in combination with hCG, LH, GnRH, GnRH analogues or estrogen might also induce ovulation in swine; natural or recombinant follicle stimulating hormone (FSH), alone or in combination with hCG, LH, GnRH, GnRH analogues or estrogen might produce ovulation; as well as various combinations of the treatments described in this paragraph.

Control of Estrus in Cycling Gilts and Sows Through Zeranol Administration

Figure 2:
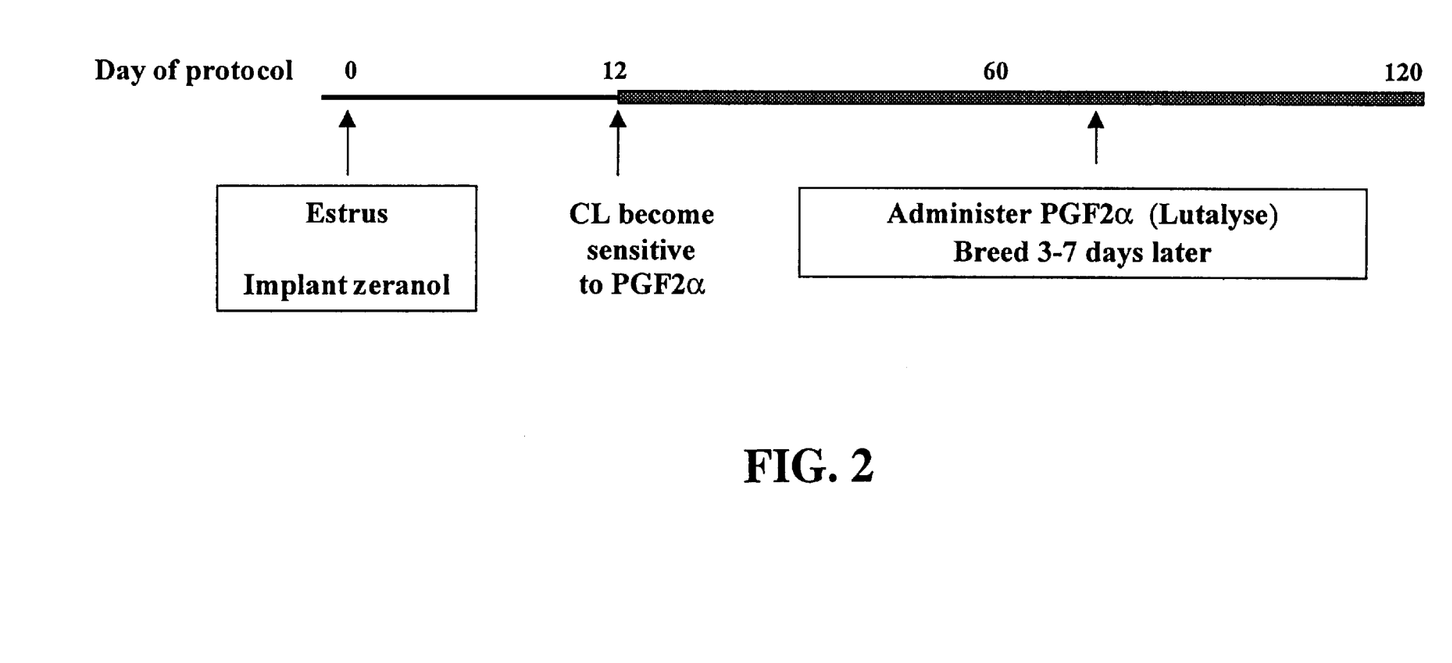

Treatment of gilts and sows experiencing estrus cycles with zeranol has different effects depending upon the day of the estrous cycle on which zeranol is administered. When zeranol is administered as an implant, it is preferably administered once in a range of about 0.01 to 150 mg, with a preferred range of about 0.1 to 80 mg, and a more preferred range of about 1 to 40 mg. When zeranol is administered orally, it is preferably administered daily in a dosage range from about 0.1 mg to 1000 mg, with a preferred range of about 0.5 mg to 300 mg, and a more preferred range of about 1.0 mg to 150 mg. If zeranol treatment is initiated before day 11 of the estrous cycle and continued (as in the case of a zeranol implant for example), the CL will be maintained by zeranol (FIG. 2). In this case zeranol will be present during the critical period of maternal recognition of pregnancy (days 11–15 of the estrous cycle). However, if zeranol treatment is initiated during the late-luteal phase of the estrous cycle (after day 11) and continued, the CL will regress and the CL of the next estrous cycle will then be maintained. Pseudopregnancy may last as long as 140 days (90 days is common). Zeranol treatment helps to ensure a long pseudopregnancy. After the second week of zeranol-induced pseudopregnancy and throughout the remainder of the pseudopregnancy, the producer can administer PG, as two separate 5–10 mg injections spaced 4 to 6 h apart to cause regression of the CL and return to estrus (FIG. 2). The females may be bred at estrus 3 to 7 days following PG.

Control of Estrus in Sows after Lactation Through Combined Administration of Zeranol and hCG Following lactation, sows exhibit some degree of estrus synchronization, assuming that they are weaned after about day 17 of lactation and are in good body condition. Currently, many producers employ early weaning strategies which wean the piglet from the dam as early as day 10 of lactation. This strategy has resulted in less reliable return to estrus in sows following weaning.

Figure 3:
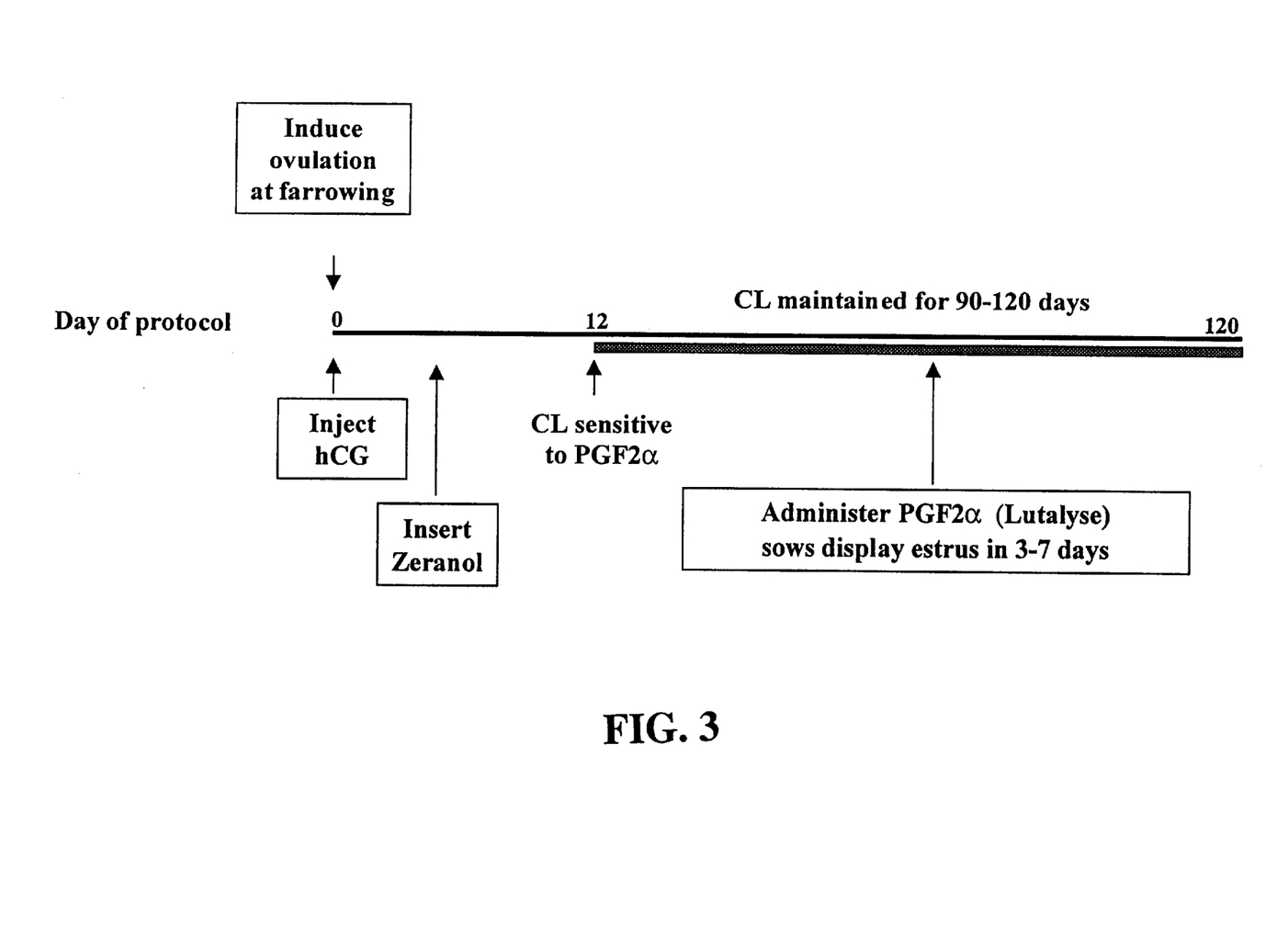

In order to promote a more reliable return to estrus in sows following weaning, sows are treated with hCG and with zeranol on the day they farrow (FIG. 3). Treatment with hCG at this time causes ovulation and CL formation in greater than 95% of all sows. Zeranol maintains these induced CL until the producer wishes to breed the sow. The CL become sensitive to regression by $PGF_2\alpha$ administration about two weeks after their formation. The producer may then administer PG as two 5 to 10 mg injections spaced 4 to 6 hours apart to regress the sow's CL. The sow displays estrus within 3 to 7 days following PG.

Reduction of the Generation Interval in Swine.

Shortening the generation interval is another object of the present invention which saves producers substantial resources expended in production costs. A modest reduction in the generation interval may be achieved by inducing a pseudopregnancy prior to first breeding. Induction of pseudopregnancy and the maintenance of CL function with zeranol is an object of the present invention. Termination of a zeranol-induced pseudopregnancy forms the basis of the present method of estrous synchronization. It has been reported that the imposition of an estrogen-induced pseudopregnancy prior to first conception resulted in increased piglet birth weights (Zavy, M. T., et al., 1988, Theriogenol. 30: 721–732). These authors theorized that prolonged exposure to physiological concentrations of progesterone, such as occurs during pregnancy or pseudopregnancy, may have resulted in improved uterine maturation and thus, improved uterine function during the subsequent pregnancy. At present, pork producers delay breeding of replacement gilts until after 200 days of age because the uterus is not considered mature until this time. Gilts bred at less than 200 days of age tend to have reduced farrowing rates. A consequence of the zeranol-induced pseudopregnancy, which we employ to synchronize estrus in prepubertal gilts, may be an advancement of uterine maturation. By employing the estrus synchronization method described herein, producers may be able to breed gilts at 170–180 days of age with no loss in fertility. The resulting 30 day reduction in the generation interval would result in feed and labor savings to the producer of about $25 per treated gilt. A more dramatic example of employing zeranol to shorten the generation interval is presented in Example 8.

Maintenance of Pregnancy and Estrous Synchronization in the Mare

In the mare, progesterone secretion by the primary CL is required to maintain pregnancy for about the first 50 to 70 days of gestation. Beginning at about day 35 of gestation, the endometrial cups secrete PMSG (i.e., equine chorionic gonadotropin, eCG). eCG induces additional multiple ovulations during pregnancy in the mare resulting in the formation of accessory or secondary CL which also produce progesterone. Together the primary and secondary CL produce the progesterone required to maintain the pregnancy until about day 150 of pregnancy when the feto-placental unit takes over progesterone production. To create a pseudopregnant condition, mares are treated with zeranol on or before day 10 of the estrus cycle. Similar to the pig, the time of maternal recognition of pregnancy in the mare is between days 11 and 16 of the estrous cycle. Thus, zeranol must be present on these days in order to mimic the embryonic signals of pregnancy and to create a pseudopregnant condition. When zeranol is administered as an implant, it is preferably administered once in a range of about 0.01 to 800 mg, with a preferred range of about 1 to 500 mg, and a more preferred range of about 10 to 100 mg. When zeranol is administered orally, it is preferably administered daily in a dosage range from about 1 mg to 5000 mg, with a preferred range of about 5 mg to 2500 mg, and a more preferred range of about 10 mg to 1000 mg. Once a pseudopregnant condition is established, the mare is brought into estrous by administering PG to regress the CL.

To help maintain pregnancy in the mare, zeranol is administered after breeding in the same dose ranges described above. Zeranol should be administered so that it will be present during the period of maternal recognition of pregnancy (days 11–16 of the estrous cycle) so as to mimic and augment the pregnancy signals produced by the embryo.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention, and/or the scope of the appended claims.

EXAMPLE 1
Induction of Pseudopregnancy in Mature Cycling Gilts with Zeranol Treatment Three gilts were implanted sc under the skin of the ear with 36 mg of zeranol before day 11 of their estrous cycle. All three gilts failed to return to estrus, and maintained elevated serum progesterone concentrations through the day of PG administration on days 23, 27 and 31 following the previous estrus. Prostaglandin $F_2\alpha$ was administered as two 10 mg im injections given about 4 to 6 hours apart. All three gilts returned to estrus within 7 days following administration of $PGF_2\alpha$.

The durations of pseudopregnancy in these gilts, in which pseudopregnancy was terminated by $PGF_2\alpha$, were 2, 6, and 10 days, respectively.

EXAMPLE 2
Maintenance of Corpora Lutea with Zeranol in Cycling Gilts and in Prepubertal Gilts Following Induced Ovulation Two prepubertal gilts and 4 cyclic gilts were treated with 1500 IU of PMSG followed 3 days later with 1000 IU hCG (both given im) to induce ovulation. Zeranol (36 mg) was implanted sc in the ear at the time of hCG administration. In the 4 cyclic gilts, 3 were implanted with zeranol (36 mg, sc in the ear) on day 6 of the estrous cycle while the remaining gilt was implanted on day 10. Treatment with PMSG and hCG induced ovulation in both prepubertal gilts as indicated by elevated serum progesterone levels. All gilts maintained their CL as evidenced by failure to return to estrus and by elevated serum progesterone concentrations at 28 days after hCG administration. Following two 10 mg injections of $PGF_2\alpha$ on day 28 after hCG treatment, gilts displayed estrus at 4.5±0.3 days. The 4 cyclic gilts displayed inter-estrous intervals of 37, 38, 38 and 42 days in duration. The 2 prepubertal gilts showed intervals from hCG to estrus of 31 and 33 days.

Figure 4:
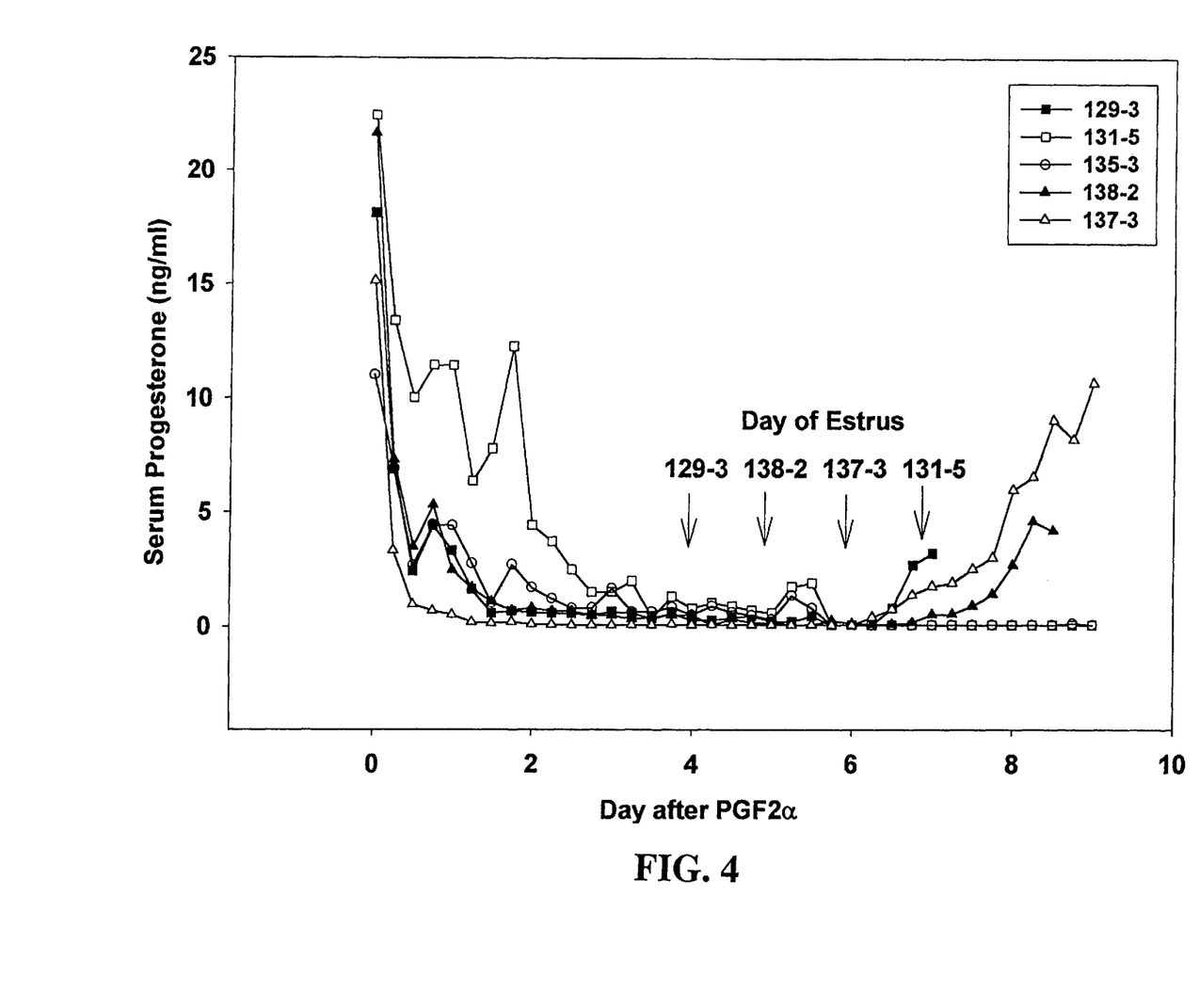
FIG. 4 demonstrates serum progesterone concentrations (ng/ml) in zeranol-induced pseudopregnant gilts in the days following treatment with PG.

EXAMPLE 3
Prostaglandin-Induced Return to Estrus in Prepubertal Gilts Made Pseudopregnant with Zeranol Five gilts, in which previous estrus cycles had not been detected, were treated with PMSG (1500 IU given im) followed 3 days later with hCG (1000 IU im) to induce ovulation. Zeranol (36 mg sc in the ear) was implanted at the time of hCG administration. Twenty eight days following hCG treatment, all gilts were treated with 2 injections of PG, 10 mg per im injection). Concentrations of serum progesterone and time of return to estrus are shown in FIG. 4. All gilts ovulated following treatment with hCG as evidenced by elevated progesterone at the time of $PGF_2\alpha$ treatment. Serum progesterone levels fell to less than 1 ng/ml in all gilts following $PGF_2\alpha$ treatment, indicating that treatment with PG resulted in the demise of the CL. Four of the 5 gilts returned to estrus within 7 days of $PGF_2\alpha$ administration. One gilt failed to display estrus after $PGF_2\alpha$ injection even though serum progesterone concentrations remained low, suggesting that this gilt became acyclic.

To date, gilts have been treated with zeranol and $PGF_2\alpha$ at least 46 times. Gilts made pseudopregnant with zeranol were treated with $PGF_2\alpha$ to regress the CL at times ranging from 2 to 35 days of apparent pseudopregnancy. All gilts which returned to estrus following PG administration did so within 7 days of treatment.

These data strongly suggest that zeranol is capable extending the life span of the CL of the pig, thereby rendering females pseudopregnant. Furthermore, the maintained CL appear to be sensitive to regression by $PGF_2\alpha$ thereby permitting the synchronization of estrus.

EXAMPLE 4
Effects of Oral Administration of Zeranol to Induce Pseudopregnancy in Prepubertal Gilts The following experiment was performed to determine whether oral administration of zeranol is capable of rendering gilts pseudopregnant and whether such oral administration is economical. On the day after their arrival at the facility, 30 prepubertal gilts (approximately 5.5 months of age and averaging 108.6±1.0 kg) received 500 IU of hCG im to induce ovulation. Gilts in the positive control group (n=6) also received 36 mg of zeranol sc as an ear implant on the day of hCG administration. Gilts fed zeranol received 12, 24, 36 or 48 mg of zeranol orally each day (n=6 per dose). Zeranol feeding was initiated at day 9 after hCG administration. Zeranol was fed for 14 days unless the gilt displayed estrus during the feeding period at which time zeranol feeding was discontinued. Zeranol feeding was timed to include the period of maternal recognition of pregnancy, i.e., days 11 to 15 of the estrous cycle. Zeranol was provided orally in the form of a vanilla wafer. The wafer contained the appropriate amount and volume of zeranol which was dissolved in ethanol and previously applied to the wafer.

At the initiation of zeranol feeding, a few gilts in each oral treatment group did not consistently eat the wafer. Zeranol feeding was discontinued in these animals, however they were implanted with 24 mg of zeranol on day 12 (n=7) after hCG treatment. The failure of several gilts to eat their zeranol wafer when offered was unexpected. The problem appeared to be one of nervous behavior rather than one of feed refusal. Gilts in the present experiment were group housed and brought individually to a separate feeding area to consume the zeranol wafer. The problem gilts appeared to be unable to adjust to this temporary separation from their companions and to focus upon eating their wafer. After 4 successive days of attempted feeding (day 9 to day 12 after hCG treatment), 7 gilts were implanted with 24 mg of zeranol on day 12. This resulted in 13 gilts implanted with zeranol and 17 gilts that received zeranol orally (Table 1).

Gilts were checked for estrus daily for 10 minutes by direct contact with a mature boar, beginning on the day of hCG administration and throughout the experiment. Gilts that were not in estrus during the "holding period" from day 8 to day 35 following hCG were treated with two 10 mg injections of $PGF_2\alpha$, sold under the trademark LUTALYSE (Pharmacia & UpJohn, Kalamazoo, Mich.) spaced 4 hours apart. Four gilts that failed to display estrus within 7 days following $PGF_2\alpha$ treatment received a second treatment with two 10 mg injections of $PGF_2\alpha$ spaced 6 hours apart.

Contrary to our expectations, 17 of 30 gilts (57%) displayed estrus on days 4 and 5 (4.5±0.1 days) after administration of hCG (Table 1). This suggests that sufficient follicular development can occur prior to ovulation in hCG-treated gilts to induce estrus behavior. While not wanting to be bound by the following statement, it seems likely that zeranol and hCG-stimulated ovarian estrogen production synergize to produce estrus behavior in prepubertal gilts simultaneously treated with hCG and zeranol.

Feeding up to 48 mg of zeranol per day did not appear to render gilts pseudopregnant (Table 1). Nine of 17 gilts fed zeranol displayed estrus during the "holding period" between 8 and 35 days after hCG administration. The average hCG-estrus interval was 27±0.8 days. Presumably, the 8 remaining fed gilts failed to continue to cycle following hCG-induced ovulation. In contrast to the results obtained in fed gilts, only 1 of 13 gilts implanted with either 24 or 36 mg of zeranol cycled during the holding period. This gilt (number 12) displayed estrus at 24 days after hCG, and had remained in a state of persistent estrus. The results demonstrate that fewer gilts implanted with zeranol cycled during the holding period than gilts fed zeranol, 7.7% vs 52.9%, p<0.05.

Four of eight zeranol-fed gilts which had not displayed estrus during the holding period displayed estrus within 7 days following the administration of $PGF_2\alpha$ on day 35 of the experiment. Although pseudopregnancy in these gilts cannot be ruled out in the absence of data on circulating concentrations of progesterone, it seems likely that these 4 gilts experienced their pubertal estrus in response to sexual maturation and continuing boar exposure. In contrast, 11 of 12 zeranol implanted gilts which had not displayed estrus during the holding period experienced estrus at 4.8±0.2 days after treatment with $PGF_2\alpha$. Overall, a greater proportion (P<0.01) of zeranol-implanted gilts (11/13, 84.6%) than zeranol-fed gilts (4/17, 23.5%) displayed normal estrus during days 38 to 42 of the experiment.

Five gilts (1 implanted with zeranol and 4 fed zeranol) failed to display estrus within 7 days following the first treatment with $PGF_2\alpha$. These gilts were treated a second time with $PGF_2\alpha$ and checked for estrus for an additional 7 days. None of these gilts displayed estrus following the second $PGF_2\alpha$ treatment, and each was classified as acyclic (Table 1).

The results of this experiment demonstrate the following: administration of a combination of hCG and zeranol will induce estrus in a significant proportion of prepubertal gilts; treatment with hCG will induce ovulation in the great majority of prepubertal gilts; feeding zeranol at up to 48 mg per day will not maintain hCG-induced CL in prepubertal gilts; implants containing as little as 24 mg of zeranol will maintain hCG-induced corpora lutea in prepubertal gilts; and treatment with $PGF_2\alpha$ will promote the lysis of the corpora lutea of zeranol-induced pseudopregnant gilts resulting in return to estrus.

TABLE 1

Effects of hCG and zeranol on expression of estrus in prepubertal gilts.

| | Zeranol Treatment Group | | | | | | | |
| --- | --- | --- | --- | --- | --- | --- | --- | --- |
| | Implant (mg) | | | Oral (mg/day) | | | | |
| Item | 36 | 24 | Totals | 12 | 24 | 36 | 48 | Totals |
| Gilts/group | 6 | 7 | 13 | 6 | 4 | 4 | 3 | 17 |
| In estrus after hCG | 4 | 2 | 6 | 2 | 3 | 4 | 2 | 11 |
| In estrus during the holding period[a] | 1 | 0 | 1 | 4 | 1 | 2 | 2 | 9 |
| In estrus 3–7 days after $PGF_2\alpha$ | 5 | 6 | 11 | 0 | 3 | 1 | 0 | 4 |
| Acyclic gilts[b] | 0 | 1 | 1 | 2 | 0 | 1 | 1 | 4 |

[a] Defined as the period 8–35 days after administration of hCG to induce ovulation.
[b] Gilts which failed to display estrus at any time throughout the experiment.

EXAMPLE 5

Examination of a Dose Range of Orally Administered Zeranol to Induce Pseudopregnancy in Mature Gilts In the experiment described in the preceding example, an oral dose of zeranol capable of rendering gilts pseudopregnant was not determined. In this experiment, a wider dose range of oral zeranol was tested.

Twenty mature gilts (about 135 kg in body weight) were checked daily for estrus for 10 days in the presence of a mature boar. At estrus, gilts were randomly assigned to one of 4 treatments: 36 mg implant of zeranol in the ear (n=4); 12 mg implant of zeranol in the ear (n=4); 36 mg zeranol orally per day (n=4); or 72 mg zeranol orally per day (n=4). In implanted gilts, zeranol was implanted on or before day 6 of the estrous cycle. In gilts fed zeranol, zeranol was given orally on days 8 through 18 of the estrous cycle. A fifth treatment group (n=4) was formed with 4 gilts which had failed to display estrus in response to 10 days of boar exposure. These gilts received 500 IU of hCG to induce ovulation and were simultaneously implanted sc with 12 mg of zeranol. For all zeranol treatments, zeranol was administered so as to be present during the period of maternal recognition of pregnancy (days 11–15 of the estrous cycle). Gilts implanted with zeranol were checked daily for estrus during a 49–54 day holding period after estrus or injection of hCG. Gilts fed zeranol were checked daily for estrus during a 31 to 35 day holding period after estrus. Gilts not displaying estrus during their respective holding periods were treated with $PGF_2\alpha$ to induce estrus. $PGF_2\alpha$ was given as two, 10 mg injections separated at an interval of 4 hours. Gilts which did not display estrus within 7 days after their first treatment with $PGF_2\alpha$ were again treated with two, 10 mg injections of $PGF_2\alpha$, separated by an interval of 6 hours, and checked for estrus for an additional 7 days.

In this experiment, no difficulties were encountered with feeding zeranol treated wafers, supporting the idea expressed in the previous example, that those gilts may have been distracted from consuming the wafer due to a separation anxiety.

During the holding period, gilts fed 36 mg of zeranol daily were not rendered pseudopregnant. All four gilts consuming this dose cycled during the holding period with an average inter-estrous interval of 22.5±2.3 days (Table 2). This agrees with the results obtained in the experiment described in the previous example, in which feeding up to 48 mg of zeranol per day failed to maintain hCG-induced corpora lutea in prepubertal gilts. In contrast, none of the gilts consuming 72 mg of zeranol per day displayed estrus during the holding period. Half of the gilts (4 of 8) implanted with 12 mg of zeranol failed to display estrus during the holding period. This was true regardless of whether the corpora lutea occurred naturally or were induced with hCG. Finally, in agreement with the results obtained in the experiment described in the preceding example, all 4 gilts implanted with 36 mg of zeranol failed to display estrus during the holding period.

All gilts fed 72 mg of zeranol per day displayed estrus within 7 days following the first administration of $PGF_2\alpha$ (Table 2). This result suggests that these gilts were rendered pseudopregnant by zeranol feeding. Regardless of the dose of zeranol, only half of the implanted gilts (4 of 8) displayed estrus within 7 days following the first treatment with $PGF_2\alpha$. Following a second round of $PGF_2\alpha$ treatment, 3 of the 4 remaining zeranol-implanted gilts displayed estrus within 7 days. These results suggest that these gilts were, in fact, pseudopregnant, but that the corpora lutea in these gilts may have been somewhat resistant to regression by $PGF_2\alpha$.

The results of this experiment demonstrate the following: feeding 72 mg of zeranol during the period of maternal recognition of pregnancy renders mature cycling gilts pseudopregnant; the minimum effective oral dose of zeranol capable of producing pseudopregnancy during the period of maternal recognition of pregnancy may be between 48 mg and 72 mg per day; and, the minimum effective implanted dose of zeranol that will produce pseudopregnancy may be between 12 and 24 mg of zeranol.

TABLE 2

Effects of zeranol on expression of estrus in gilts.

| | Zeranol Treatment Group | | | | |
|---|---|---|---|---|---|
| | Oral (mg/day) | | Implant (mg) | | |
| Item | 36 | 72 | hCG + 12 | 12 | 36 |
| Gilts/group | 4 | 4 | 4 | 4 | 4 |
| In estrus during the holding period[a] | 4 | 0 | 2 | 2 | 0 |
| Responding to First $PGF_2\alpha$ | — | 4 | 1 | 1 | 2 |
| Responding to Second $PGF_2\alpha$ | — | — | 1 | 1 | 1 |
| Non-responsive[b] | 0 | 0 | 0 | 0 | 1 |

[a]The 31 to 35 day period after estrus in gilts fed zeranol. The 49 to 54 day period after estrus or injection of hCG in gilts implanted with zeranol.
[b]Failed to display estrus after 2 rounds of PG treatment.

EXAMPLE 6

Examination of Length of Pseudopregnancy in Sows Treated with Zeranol

The following experiment is in progress at the time of the filing of this patent application. Six mature sows (at least 15 months of age and weighing more than 400 lb) were implanted with 24 mg of zeranol sc in the ear at estrus. One additional sow was not treated with zeranol. All sows were checked for estrus once daily in direct contact with a mature boar. Four of six zeranol-treated sows have, thus far, failed to show estrus for more than 90 days following zeranol administration. However, two zeranol treated sows displayed interestrous intervals of 23 and 31 days. These two sows were re-implanted with an additional 24 mg of zeranol at estrus. Thus far, these two retreated sows have not displayed estrus for more than 60 days following their second zeranol treatment. During this same period, the one untreated sow has displayed estrus a total of 5 times at regular 18 to 21 day intervals. These data demonstrate that a state of prolonged pseudopregnancy can be induced in mature sows by treatment with zeranol.

EXAMPLE 7

Inducing Pseudopregnancy and Synchronizing Estrus in Gilts of Unknown Reproductive Status In the pig, corpora lutea are induced at nearly any stage of the estrus cycle by the administration of appropriate gonadotropins. The administration of PMSG (800–1500 IU) followed 3 to 4 days later by hCG (500–1000 IU) reliably induces ovulation and subsequent formation of CL. The administration of a combination of PMSG (400–1200 IU) and hCG (200–600 IU) or of PMSG (1000–2000 IU) or hCG alone (500–1000 IU) induces ovulation and CL formation as well. These gonadotropin-induced CL are maintained by treatment with an appropriate dose of zeranol. When zeranol is administered as an implant, it is preferably administered once in a range of about 0.01 to 150 mg, with a preferred range of about 0.1 to 80 mg, and a more preferred range of about 1 to 40 mg. When administered orally, zeranol is preferably administered daily in a dosage range from about 0.1 mg to 1000 mg, with a preferred range of about 0.5 mg to 300 mg, and a more preferred range of about 1.0 mg to 150 mg. Zeranol is administered so that is will be present on days 11 through 15 after induced ovulation. A simple method is to implant females with zeranol on the day when they receive gonadotropin treatment to induce ovulation. In this manner, it is not necessary to know the stage of the estrous cycle at which gilts are treated or whether treated gilts are cycling at all. In prepubertal gilts, gonadotropins induce ovulation and the resulting CL is maintained by zeranol. In cycling gilts treated with zeranol before day 11 of the estrous cycle, zeranol maintains both the naturally occurring CL and the CL induced by gonadotropin treatment. In cycling gilts treated with zeranol after day 11 of the estrous cycle, zeranol maintains the CL induced by gonadotropin treatment while the naturally occurring CL likely regresses. Once CL are maintained by zeranol, the administration of PG regresses the CL and induces estrus as desired.

EXAMPLE 8

Shortening the Generation Interval Through Zeranol Administration

Unlike estradiol, zeranol maintains gonadotropin-induced CL in gilts as young as 90 days of age. As such, the generation interval (age at first breeding) may be reduced in swine by breeding gilts at a younger age than is currently possible. Ovulation is induced in prepubertal gilts as young as 90 days of age by administering 500 to 1500 IU of PMSG im followed 48 to 72 hours later by injection of 500 IU of hCG im. The administration of a combination of PMSG (400 to 1200 IU) and hCG (200 to 600 IU) or of PMSG (1000 to 2000 IU) or hCG alone (500 to 1000 IU) also induces ovulation. Gilts are then bred between 12 to 24 hours prior to gonadotropin-induced ovulation. Bred gilts are treated so as to provide sufficient zeranol between days 11 and 15 after induced ovulation to maintain the CL of pregnancy. When zeranol is administered as an implant, it is preferably administered once in a range of about 0.01 to 150 mg, with a preferred range of about 0.1 to 80 mg, and a more preferred range of about 1 to 40 mg. When zeranol is administered orally, it is preferably administered daily in a dosage range from about 0.1 mg to 1000 mg, with a preferred range of about 0.5 mg to 300 mg, and a more preferred range of about 1.0 mg to 150 mg. Gilts bred at 4 months of age, in which pregnancies are maintained by zeranol, give birth to their first litter at about 8 months of age. This represents a 4 month, 33% reduction in the generation interval. At a cost of about $0.83 per day in feed and labor to maintain breeding females, a 4 month reduction in the time to her first litter represents a savings to the producer of about $100 per treated gilt. This strategy can also be employed in older gilts, provided they are prepubertal at the time of treatment. Producers benefit from any reduction in the age of first breeding which is presently at about 200 to 220 days of age.

EXAMPLE 9

Maintaining Pregnancy, Enhancing Farrowing Rates and Treating Summer Infertility Through Zeranol Administration Reduced farrowing rates in gilts and sows are common during the early summer months. This may be due in part to a failure of the dam to recognize the embryonic signals produced by an otherwise normal pregnancy (Love R. J., et al., 1993, J. Reprod. Fertil. (Suppl. 48):191–206). Zeranol treatment may augment these embryonic signals and help to maintain pregnancy. Gilts and sows are treated with zeranol so that it will be present during the period of maternal recognition of pregnancy (days 11–15 after estrus). When zeranol is administered as an implant, it is preferably administered once in a range of about 0.01 to 150 mg, with a preferred range of about 0.1 to 80 mg, and a more preferred range of about 1 to 40 mg. When zeranol is administered orally, it is preferably administered daily in a dosage range from about 0.1 mg to 1000 mg, with a preferred range of about 0.5 mg to 300 mg, and a more preferred range of about 1.0 mg to 150 mg. Zeranol treatment helps to maintain CL function and pregnancy in bred females. In addition, zeranol treatment induces a pseudopregnancy in females which do not become pregnant after breeding. Females diagnosed as non-pregnant are then treated with PG to terminate pseudopregnancy and to induce estrus within 3–7 days. Thus, females that are bred but that do not become pregnant can be rebred in a synchronized manner in order to fit into a subsequent farrowing group.

Bred females are also treated with zeranol in order to mimic some, but not all, of the signals of pregnancy. This is accomplished by initiating treatment with zeranol on days 13 or 14 after breeding. Non-pregnant females treated in this manner are not likely to become pseudopregnant since zeranol treatment is initiated too late to mimic all of the required signals of pregnancy. Non-pregnant females then return to estrus without treatment with PG. However, in pregnant females, maintenance of pregnancy is enhanced via augmentation of some of the signals of pregnancy by zeranol.

The strategies outlined above can be applied at any time of year (not just the summer months) in order to help maintain pregnancy and to enhance farrowing rates. For example, treatment with zeranol will be particularly useful in maintaining pregnancy in females stressed by shipping or mixing during early pregnancy.

EXAMPLE 10

Maintenance of pregnancy established during lactation in sows

The number of pigs produced per sow per year is increased by reducing the number of days sows spend recovering following lactation before they are rebred. Ovulation is induced during lactation by the administration of gonadotropins, particularly when sows are treated with gonadotropins later than day 14 after parturition. Furthermore, sows which are bred following this induced ovulation appear to conceive normally. However, only about 65% of these sows farrow. While not wanting to be bound by the following statement, the low farrowing rate in sows which are bred during lactation may be due to a reduced ability of the dam to perceive the embryonic signals produced on days 11 to 15 of pregnancy and/or to a greater susceptibility of induced CL to regression by endogenous uterine prostaglandin secretion. In either case, treatment with zeranol helps to maintain pregnancies established during lactation in the sow. On day 10 or later after parturition, sows are treated with PMSG (1000–3000 IU), followed 48 to 72 h later by hCG (500–1000 IU) to induce follicular development and ovulation. Again, the administration of a combination of PMSG (400–3000 IU) and hCG (200–1000 IU), or of PMSG (1000–3000 IU) or hCG alone (500–1000 IU), may also induce ovulation. Sows are then be bred 12–24 hours before ovulation. Sows are treated with zeranol so that it will be present during the period of maternal recognition of pregnancy (days 11–15 of the induced estrous cycle). When zeranol is administered as an implant, it is preferably administered once in a range of about 0.01 to 150 mg, with a preferred range of about 0.1 to 80 mg, and a more preferred range of about 1 to 40 mg. When zeranol is administered orally, it is preferably administered daily in a dosage range from about 0.1 mg to 1000 mg, with a preferred range of about 0.5 mg to 300 mg, and a more preferred range of about 1.0 mg to 150 mg. Thus, maintenance of CL function and of pregnancy is enhanced in pregnant sows. However, a pseudopregnancy is induced in bred sows which fail to become pregnant. Therefore, bred sows that are diagnosed as non-pregnant are treated with PG to terminate pseudopregnancy and to induce estrus within 3-7 days.

It may prove more desirable to treat bred sows with zeranol so as to mimic only some of the signals of pregnancy. This is accomplished by initiating treatment with zeranol on days 13 or 14 after breeding. Non-pregnant sows treated in this manner are not likely be made pseudopregnant since zeranol treatment is initiated too late to mimic all of the signals of pregnancy. Non-pregnant sows, therefore, return to estrus without treatment with PG. However, in pregnant sows, maintenance of pregnancy is enhanced via augmentation of some of the signals of pregnancy with zeranol.

The invention has been described in detail with particular reference to certain embodiments, but variations and modifications can be made without departing from the spirit and the scope of the present invention as defined in the appended claims.

I claim:

1. A method for modulating a function of a female reproductive system comprising administration to a female animal of an effective amount of a composition comprising zeranol.

2. The method of claim 1 wherein the function of the female reproductive system comprises corpus luteum function, progesterone secretion, progesterone synthesis, induction of pseudopregnancy, maintenance of pregnancy, onset of puberty, maturation of the uterus, maintenance of uterine endometrium, return to estrus, onset of fertility, maintenance of fertility, return to fertility following lactation, return to fertility following parturition, decrease in durations of infertile periods, and summer infertility.

3. The method of claim 1, wherein the female animal is a domestic animal, a farm animal or a laboratory animal.

4. The method of claim 1, wherein the female animal is a pig, feral pig, peccary, horse, bear, hippopotamus, lion, tiger, elephant, rhinoceros, rat, mouse, hamster, guinea pig, cat, sheep, or cow.

5. The method of claim 1, wherein the female animal is a pig or a horse.

6. The method of claim 1, wherein the administration comprises parenteral, topical, or oral administration.

7. The method of claim 1, wherein the effective amount of the composition is between approximately 0.01 mg and 800 mg of zeranol and is administered as an implant.

8. The method of claim 1, wherein the female animal is a pig and the effective amount of the composition is between approximately 0.01 mg and 150 mg of zeranol and is administered as an implant.

9. The method of claim 1, wherein the effective amount of the composition is between approximately 0.1 mg and 5000 mg of zeranol and is administered orally.

10. The method of claim 1, wherein the female animal is a pig, the administration is oral, and the effective amount of the composition is an amount is between approximately 0.1 mg and 1000 mg of zeranol.

11. The method of claim 1 further comprising administration of one or more substances selected from the group consisting of prostaglandin, prostaglandin $F_2\alpha$, luteinizing hormone, follicle stimulating hormone, gonadotropin, pregnant mare's serum gonadotropin, chorionic gonadotropin, human chorionic gonadotropin, equine chorionic gonadotropin, gonadotropin releasing hormone, neuropeptide Y, estrogen, progesterone, analogs thereof, and combinations thereof.

12. The method of claim 1 further comprising administration of gonadotropin prior to zeranol administration and prostaglandin administration after zeranol administration.

* * * * *